US012571708B2

(12) United States Patent
Donnat et al.

(10) Patent No.: US 12,571,708 B2
(45) Date of Patent: Mar. 10, 2026

(54) METHOD FOR CALCULATING A STREAM OF AT LEAST ONE GAS EMITTED BY A SOURCE INTO THE ATMOSPHERE, MEASUREMENT METHOD, AND ASSOCIATED SYSTEM AND KIT

(71) Applicants: Centre national de la recherche scientifique, Paris (FR); UNIVERSITE DE REIMS CHAMPAGNE-ARDENNE, Reims Cedex (FR); TotalEnergies OneTech, Courbevoie (FR)

(72) Inventors: Ludovic Donnat, La Motte Servolex (FR); Olivier Duclaux, Eyzin Pinet (FR)

(73) Assignees: Centre national de la recherche scientifique, Paris (FR); UNIVERSITE DE REIMS CHAMPAGNE-ARDENNE, Reims Cedex (FR); TotalEnergies OneTech, Courbevoie (FR)

( * ) Notice: Subject to any disclaimer, the term of this patent is extended or adjusted under 35 U.S.C. 154(b) by 663 days.

(21) Appl. No.: 17/917,723

(22) PCT Filed: Apr. 8, 2021

(86) PCT No.: PCT/EP2021/059173
§ 371 (c)(1),
(2) Date: Oct. 7, 2022

(87) PCT Pub. No.: WO2021/204941
PCT Pub. Date: Oct. 14, 2021

(65) Prior Publication Data
US 2023/0160789 A1 May 25, 2023

(30) Foreign Application Priority Data
Apr. 8, 2020 (FR) ...................................... 2003527

(51) Int. Cl.
*G01N 1/00* (2006.01)
*B64C 39/02* (2023.01)
(Continued)

(52) U.S. Cl.
CPC ......... *G01N 1/2273* (2013.01); *B64C 39/024* (2013.01); *B64U 20/80* (2023.01); *G01N 33/0027* (2013.01); *B64U 2101/35* (2023.01)

(58) Field of Classification Search
CPC .. G01N 1/2273; G01N 33/0027; B64U 20/80; B64C 39/024
See application file for complete search history.

(56) References Cited

U.S. PATENT DOCUMENTS 3,780,566 A † 12/1973 Smith
4,135,092 A * 1/1979 Milly ................. G01N 33/0031
250/338.5
(Continued)

FOREIGN PATENT DOCUMENTS

CN 208915442 U 5/2019
EP 3100022 A1 12/2016
(Continued)

OTHER PUBLICATIONS

Rapport De Recherche Préliminaire issued in French Patent Application No. 2003527 dated Dec. 14, 2020.
(Continued)

*Primary Examiner* — Jamel E Williams
(74) *Attorney, Agent, or Firm* — Troutman Pepper Locke LLP

(57) ABSTRACT
This method comprises the following steps retrieving data about amounts of at least one gas, said data being measured in the atmosphere at a distance from the source along a plurality of lines parallel to a first direction; integrating the amounts read on each line in the first direction in order to
(Continued)

obtain an integrated overall amount on each line; integrating the product of the integrated overall amounts on each line and a wind speed present on the line in a second direction perpendicular to the first direction, in order to obtain a raw flow of gas; determining the flow of gas emitted by the source based on the raw flow of gas.

20 Claims, 8 Drawing Sheets

(51) Int. Cl.

| | |
|---|---|
| *B64U 20/80* | (2023.01) |
| *G01N 1/22* | (2006.01) |
| *G01N 33/00* | (2006.01) |
| *B64U 101/35* | (2023.01) |

(56) References Cited

U.S. PATENT DOCUMENTS

| | | | | |
|---|---|---|---|---|
| 6,509,566 | B1 † | 1/2003 | Wamsley | |
| 8,294,899 | B2 | 10/2012 | Wong | |
| 10,203,311 | B2 | 2/2019 | Risk et al. | |
| 10,704,981 | B2 | 7/2020 | Choudhury et al. | |
| 10,753,864 | B2 | 8/2020 | Kasten et al. | |
| 10,816,458 | B2 | 10/2020 | Kasten et al. | |
| 11,079,366 | B2 | 8/2021 | Klein et al. | |
| 2002/0005955 | A1 † | 1/2002 | Kramer | |
| 2003/0189711 | A1 † | 10/2003 | Orr | |
| 2012/0092649 | A1 * | 4/2012 | Wong | G01W 1/00 356/72 |
| 2013/0044314 | A1 † | 2/2013 | Koulikov | |
| 2015/0275114 | A1 † | 10/2015 | Tumiatti | |
| 2016/0214715 | A1 * | 7/2016 | Meffert | B64U 20/87 |
| 2017/0307519 | A1 † | 10/2017 | Black | |
| 2018/0059003 | A1 † | 3/2018 | Jourdainne | |
| 2018/0188129 | A1 | 7/2018 | Choudhury et al. | |
| 2019/0025199 | A1 † | 1/2019 | Koulikov | |
| 2019/0301931 | A1 | 10/2019 | Ng et al. | |
| 2019/0331652 | A1 † | 10/2019 | Ba | |
| 2021/0055180 | A1 | 2/2021 | Thorpe et al. | |
| 2021/0109074 | A1 | 4/2021 | Smith et al. | |
| 2021/0140934 | A1 | 5/2021 | Smith et al. | |
| 2021/0190745 | A1 | 6/2021 | Buckingham et al. | |
| 2021/0255158 | A1 | 8/2021 | Smith et al. | |
| 2021/0364427 | A1 † | 11/2021 | Smith | |
| 2021/0380272 | A1 | 12/2021 | Parrott et al. | |
| 2021/0382475 | A1 | 12/2021 | Smith et al. | |

FOREIGN PATENT DOCUMENTS

| | | | | |
|---|---|---|---|---|
| FR | 3 108 726 A1 | 10/2021 | | |
| WO | 2019246280 | † 12/2019 | | |
| WO | WO-2019246280 A1 | * 12/2019 | | B64D 47/00 |
| WO | 2020007684 | † 1/2020 | | |
| WO | 2020/206006 A1 | 10/2020 | | |
| WO | 2021/026215 A1 | 2/2021 | | |
| WO | 2021/055902 A1 | 3/2021 | | |
| WO | 2021158916 | † 8/2021 | | |
| WO | 2022/016107 A1 | 1/2022 | | |

OTHER PUBLICATIONS

Rapport De Recherche Internationale issued in International Patent Application No. PCT/EP2021/059173 dated Jul. 7, 2021.

Carn, S. A., "Gas. Plume and Thermal Monitoring" Chapter 65, The Encyclopedia of Volcanoes 1125-1149 (2015).

Gerlach, T. M., et al. "Application of the Li-COR CO2 analyzer to volcanic plumes" A case study, volcan Popocatépetl, Mexico, Jun. 7 and 10, 1995 Journal of Geophysical Research 102(B4):8005-8019 (1997).

Wardell, L. J., et al. "Carbon dioxide and carbon monoxide emission rates from an alkaline intra-plate volcano: Mt. Erebus, Antarctica" Journal of Volcanology and Geothermal Research 131:109-121 (2004).

Neumann, P., et al. "Micro-Drone for the Characterization and Self-Optimizing Search of Hazardous Gaseous Substance Sources: a new Approach to determine Wind Speed and Direction" IEEE 1-6 (2010).

Coburn, S., et al. "Continuous regional trace gas source attribution using a field-deployed dual frequency comb spectrometer" 18 pages (2017).

Cossel, K. C., et al. "Open-path dual-comb spectroscopy to an airborne retroreflector" Optica 4(7):724-728 (2017).

Joly, L., et al. "Atmospheric Mesaurements by Ultra-Light Spectrometer (AMULSE) Dedicated to Vertical Profile in Situ Measurements of Carbon Dioxide (CO2) Under Weather Balloons: Instrumental Development and Field Application" Sensors 16(1609):1-14 (2016).

Joly, L., et al. "The evolution of AMULSE (Atmospheric Measurements by Ultra-Light Spectrometer) and its interest in atmospheric applications. Results of the Atmospheric Profiles of Greenhouse gasEs (APOGEE) weather balloon release campaign for satellite retrieval validation" Atmospheric Measurement Techniques 1-28 (2019).

Khan, A., et al. "Low Power Greenhouse Gas Sensors for Unmanned Aerial Vehicles" Remote Sens. 4:1355-1368 (2012).

Zhang, W., et al. "Adaptive cavity-enhanced dual-comb spectroscopy" Photonics Research 7(8):883-889 (2019).

WO 2021067844 A1 , published Apr. 8, 2021. WIPO Country code not available in Patent Center as an option for foreign publications.†

WO 2020/206006 A1, published Oct. 8, 2020. WIPO Country code not available in Patent Center as an option for foreign publications.†

WO 2019/246283 A1, published Jan. 23, 2020. WIPO Country code not available in Patent Center as an option for foreign publications.†

WO 2019/246280 A1. published Dec. 26, 2019. WIPO Country code not available in Patent Center as an option for foreign publications.†

Lilian Joly, The evolution of AMULSE (Atmospheric Measurements by Ultra-Light Spectrometer) and its interest in atmospheric applications. Results of the Atmospheric Profiles of Greenhouse gasEs (APOGEE) weather balloori release campaign for satellite retrieval validation, p. 1-28, Sep. 25, 2019, Atmospheric Measurement Techniques Discussion.†

\* cited by examiner

† cited by third party

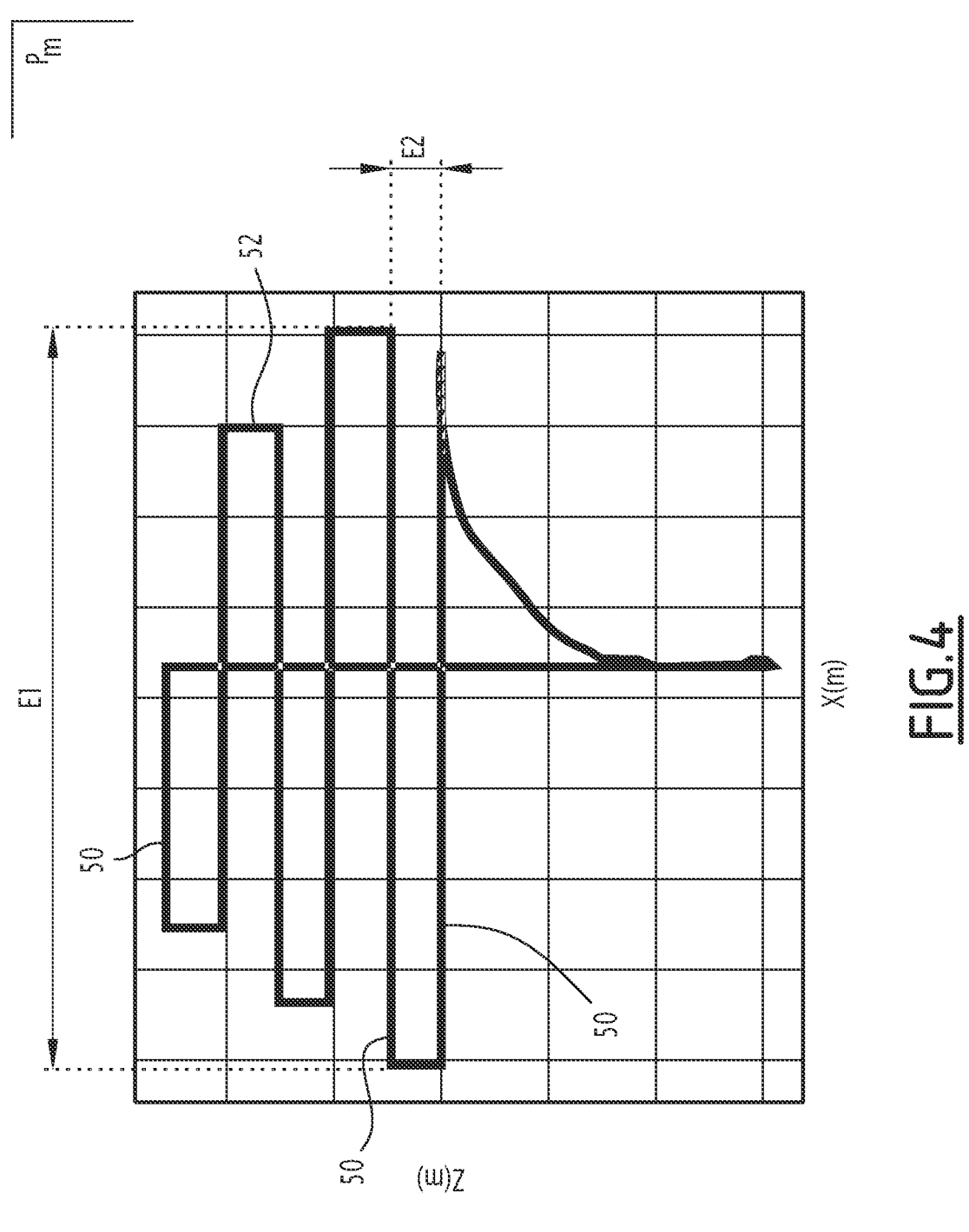
_FIG.4_

METHOD FOR CALCULATING A STREAM OF AT LEAST ONE GAS EMITTED BY A SOURCE INTO THE ATMOSPHERE, MEASUREMENT METHOD, AND ASSOCIATED SYSTEM AND KIT

CROSS REFERENCE TO RELATED APPLICATIONS

The present application is a U.S. National Phase Application under 35 U.S.C. § 371 of International Patent Application No. PCT/EP2021/059173 filed Apr. 8, 2021, which claims priority of French Patent Application No. 20 03527 filed Apr. 8, 2020. The entire contents of which are hereby incorporated by reference.

FIELD OF THE INVENTION

The present invention relates to a method for computing a flow of at least one gas emitted by a source into the atmosphere, implemented by a computing system.

BACKGROUND

The gases to be measured are especially greenhouse gases such as methane or carbon dioxide.

Preoccupations regarding protection of the environment have contributed to reinforcement of legislation on polluting emissions, especially in Europe.

Thus, industrial units, such as present in the petroleum or chemical industry, must adapt to increasingly demanding environmental constraints.

In particular, greenhouse gases are emitted during operations of extracting, transporting, refining and storing hydrocarbons. These emissions are tracked by operators and are regularly subject to reduction measures.

It is in particular necessary to characterize the sources of these greenhouse gases and the amounts of greenhouse gases emitted by these sources, with a view to ensuring that they are controlled and to reporting progress made.

However, the techniques used to identify sources of greenhouse gases and quantify diffuse and short-lived emissions are still not entirely satisfactory.

Specifically, these emissions are very difficult to measure, because they are often unchannelled, and potentially located close to pools or lakes or inaccessible locations, for example at height or at the centre of the unit in question.

One major difficulty in evaluating the emissions of a point source within an installation is often the difficulty or even the inability to get as close as possible to the source in order to measure the flow of gas emitted by the source into the atmosphere. Furthermore, given wind, the flow of gas produced by the source disperses and propagates into the atmosphere in the form of a plume. Measuring the emissions emitted by a point source is therefore generally difficult and inaccurate when at a distance from the source.

SUMMARY

One aim of the invention is to provide a method for computing the flow of at least one gas emitted by a source into the atmosphere, in particular a greenhouse gas, the method not requiring any data taken as close as possible to the source, while still being accurate and easy to implement.

To this end, one subject of the invention is a method of the abovementioned type, comprising the following steps:

retrieving data about amounts of at least one gas, said data being measured in the atmosphere at a distance from the source along a plurality of lines parallel to a first direction;

integrating the amounts read on each line in the first direction in order to obtain an integrated overall amount on each line;

integrating the product of the integrated overall amounts on each line and a wind speed present on the line in a second direction perpendicular to the first direction, in order to obtain a raw flow of gas;

determining the flow of gas emitted by the source based on the raw flow of gas.

The method according to the invention may comprise one or more of the following features, alone or in any technically possible combination:

the method comprises, between the integration steps, a step of interpolating a curve of integrated overall amounts as a function of a coordinate in the second direction, based on the computed integrated overall amounts;

the interpolation is carried out using a cubic interpolation, in particular using a piecewise cubic interpolation;

the method comprises a preliminary step of retrieving data about wind speeds present on each line;

the method comprises a preliminary step of determining an average wind common to all of the lines;

the method comprises, after the step of retrieving the amount data, computing a continuous background of gas present in the atmosphere and processing the amount data in order to eliminate the continuous background;

determining the continuous background comprises, for each line, computing an average value of amounts, measured on the line, and then eliminating amounts above the average value, and repeating the previous steps until the difference between two successive average values is less than a convergence threshold;

the first direction is horizontal, the second direction being vertical;

the flows of at least two gases emitted by the source are computed.

Another subject of the invention is a method for measuring emissions of a source into the atmosphere, comprising the following steps:

collecting amounts of at least one gas in the atmosphere at a distance from the source along a plurality of lines parallel to a first direction by flying a drone equipped with an assembly for measuring data representative of amounts of at least one gas;

transferring the collected representative data to a computing system;

using the computing system to implement the computing method as defined above.

The measuring method according to the invention may comprise one or more of the following features, alone or in any technically possible combination:

the method comprises a preliminary step of determining a wind direction and/or a configuration of an emission plume downstream of the source, the drone being flown based on the predetermined plume configuration.

the method comprises a step of measuring the wind speed.

Another subject of the invention is a system for computing a flow of at least one gas emitted by a source into the atmosphere, comprising:

a module for obtaining data about amounts of at least one
gas, said data being measured in the atmosphere at a
distance from the source along a plurality of lines
parallel to a first direction;

a module for integrating the amounts read on each line in
the first direction in order to obtain an integrated
overall amount on each line;

a module for integrating the product of the integrated
overall amounts on each line and a wind speed present
on the line in a second direction perpendicular to the
first direction, in order to obtain a raw flow of gas;

a module for determining the flow of gas emitted by the
source based on the raw flow of gas.

Another subject of the invention is a kit for measuring the
emissions of at least one gas by a source into the atmosphere,
comprising:

a drone, able to fly in the atmosphere at a distance from
the source along a plurality of lines parallel to a first
direction;

the drone being able to measure data representative of
amounts of at least one gas along each line parallel to
the first direction;

a computing system as defined above, able to receive the
representative data measured by the drone.

The kit according to the invention may comprise one or
more of the following features, alone or in any technically
possible combination:

the drone is able to continuously measure data represen-
tative of the amounts of at least two gases present in the
atmosphere.

BRIEF DESCRIPTION OF THE DRAWINGS

The invention will be better understood on reading the
following description, which is given merely by way of
example, and with reference to the appended drawings, in
which:

FIG. 4 is a view of the flight plan implemented by the
drone of the kit from FIG. 1;

DETAILED DESCRIPTION

Figure 1:
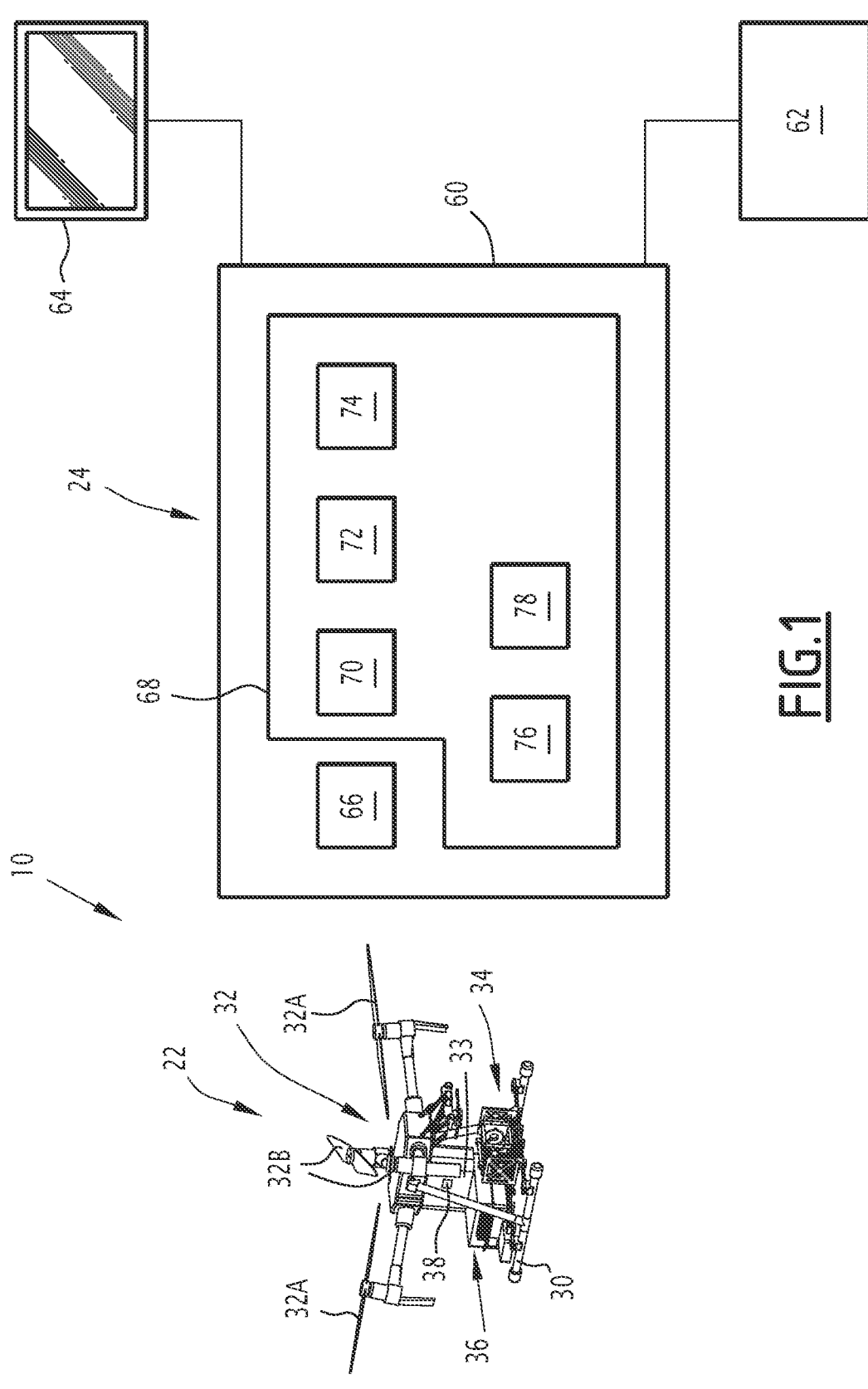
FIG. 1 is a schematic view of a first emissions measure-
ment kit according to the invention.

A kit 10 for measuring emissions of at least one gas
emitted by a source into the atmosphere is illustrated sche-
matically in FIG. 1. The kit 10 is intended to implement a
method for measuring emissions of an industrial installation
12, shown schematically in FIG. 2.

Preferably, the emission of at least two gases present in
the atmosphere is measured by the method according to the
invention. The gases are preferably methane and carbon
dioxide.

In some variants, other gases may be measured, such as
aromatic gases, especially benzene or even 1,3-butadiene,
carbon monoxide, ethane and more generally volatile
organic compounds.

The industrial installation 12 is in particular a petroleum
installation, in particular a hydrocarbon extraction, transpor-
tation, refining, processing or storage installation located at
sea or on land. The installation 12 comprises at least one
source 14 emitting gases the amount of which is measured.

Figure 3:
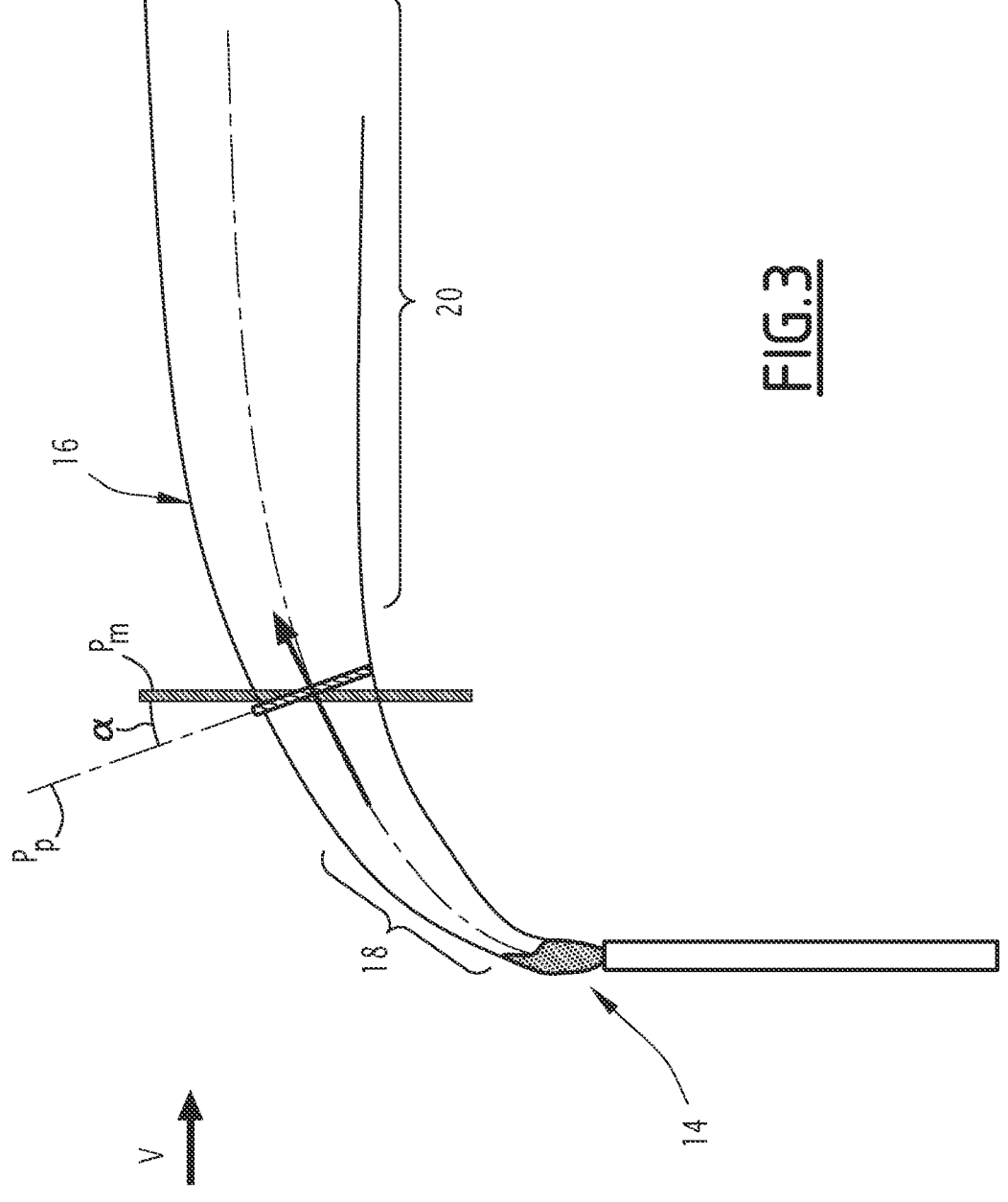
FIG. 3 is a detailed view of the plume resulting from the
source emitting in established wind conditions.

In the example shown in FIG. 3, the source 14 is a flare.
It emits gases in a plume 16 that is released from the source
14 and that propagates under the effect of the wind V.

The plume 16 is entrained by the wind V blowing in the
atmosphere close to the source 14. It advantageously has an
area 18 in which the plume 16 rises, which is substantially
vertical, and an area 20 in which the plume propagates,
which is substantially horizontal in this example.

Figure 8:
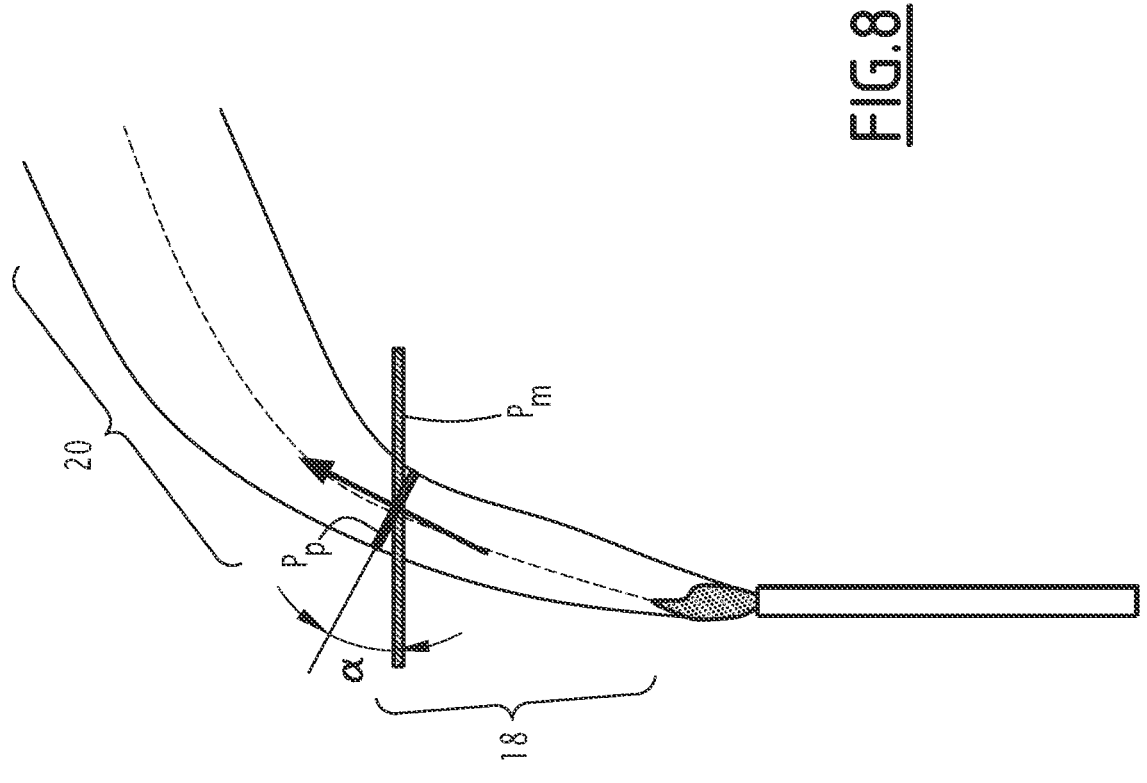
FIG. 8 is a view similar to FIG. 3, in the case of an
emission in low-wind conditions.

In the example of FIG. 8, if the wind V is lower, the rise
area 18 is higher and the propagation area 20 extends in a
manner inclined with respect to the horizontal.

With reference to FIG. 1, in order to implement the
measuring method, the measurement kit 10 comprises a
drone 22 for collecting data representative of amounts of at
least one gas, preferably of at least two gases, at a plurality
of positions in the atmosphere, at a distance from the source
14.

The kit 10 furthermore comprises a computing system 24,
able to implement a method for computing a flow of the or
of each gas emitted by the source 14 into the atmosphere,
based on data representative of amounts of each gas in the
atmosphere as measured by the drone 22.

The drone 22 is able to carry out the measurements
needed to collect data representative of the amounts of at
least one gas present in the plume 16, at a distance from the
source 14. It comprises a chassis 30, and a propelling
assembly 32, which is able to allow the chassis 30 to take off
away from the ground and it to move by flying through the
atmosphere above the ground.

The drone 22 furthermore comprises a measuring assem-
bly 34, a control assembly 36 for controlling the measuring
assembly 34, and preferably a remote transmission system
38.

With reference to FIG. 1, the propelling assembly 32
comprises a plurality of propelling members 32A, which
here are propellers driven to rotate by a motor.

The propelling assembly 32 furthermore comprises a
power source 32B, formed here by a battery, and a system
33 for locating and for controlling the movement of the
drone 22 through the atmosphere.

In this example, the drone 22 is a multi-rotor rotary-wing
drone. It does not have any fixed wings, its lift being
generated by the propelling assembly 32.

The drone 22 is for example a rotary-wing quadcopter
drone, and especially a DJI M200 drone as sold by DJI.

The propelling assembly 32 comprises a plurality of
propellers that rotate about substantially vertical axes. "Sub-
stantially vertical" is generally understood to mean that the
axes of rotation of the propellers are inclined by less than
30° with respect to the vertical.

When the motors of the propellers are supplied with
electric power by the battery, the propellers are driven to
rotate about their axis, driving a downward flow of air.

The locating and control system 33 comprises a position
sensor, especially a GPS and/or an inertial measurement
unit. It furthermore comprises a control unit, which is able
to control the movement of the drone 22 along a path pre-recorded before the flight and loaded into the system 33, or remotely and manually via a remote control.

The drone 22 is thus able to automatically follow a predefined path, or, alternatively, to be controlled manually by an operator, in order to implement a flight plan.

Preferably, in order to implement the measuring method, the drone 22 is able to take a path following a ladder-shaped movement, as illustrated by FIG. 4.

The drone 22 moves along a plurality of lines 50 parallel to a first direction D1, with a connecting segment 52 between each pair of adjacent parallel lines 50. The connecting segment 52 follows a second direction D2 transverse to the first direction D1.

Here, the first direction D1 is a horizontal direction and the second direction D2 is a vertical direction.

In this example, all of the parallel lines 50 scanned by the drone 22 extend substantially in one and the same vertical measuring plane Pm.

The extent E1 of the lines 50 in the first direction D1 is chosen based on the width of the plume 16, in order to scan the entire plume 16. This extent E1 is generally greater than 20 m and is between 20 m and 500 m.

The distance between the lines 50 is defined by an extent E2 of the connecting segments 52 in the second direction. This extent E2 is for example greater than 1 m and in particular between 1 m and 50 m.

The measuring assembly 34 comprises at least one sensor able to carry out measurements of data representative of amounts of at least one gas present in the atmosphere, at a plurality of points along each line 50.

Preferably, the data representative of the amounts of at least two gases are collected by the measuring assembly 34 along each line 50.

The measurements are carried out continuously along the line 50. The measurement frequency of data representative of each gas amount is for example greater than 1 Hz and in particular between 1 Hz and 100 Hz.

One example of a measuring assembly 34 is described in application no. 20 03027 from the Applicant, filed at the Institut National de la Propriété Industrielle in France, entitled "Drone for measuring data representative of amounts of at least two gases present in the atmosphere away from the ground and associated measuring method".

The control system 33 comprises a data collection unit that comprises at least one memory able to store the data representative of each amount of each gas, in association with the geographical position along each line 50.

The data collection unit is connected to the remote transmission system 38 in order to allow the data to be exported to the computing system 24 when the drone is flying or after the drone has flown.

The computing system 24 is located on the ground here. It comprises at least a computer 60 and a human-machine interface comprising a control member 62 such as a keyboard, a mouse and/or a touchscreen, the human-machine interface also comprising a display 64, in particular a screen.

The computer 60 comprises, as is known, at least a processor 66 and a memory 68 comprising software modules able to be executed by the processor 66 in order to carry out functions. As a variant, the computer 60 comprises programmable logic components or dedicated integrated circuits intended to carry out the functions of the modules that will be described below.

Figure 5:
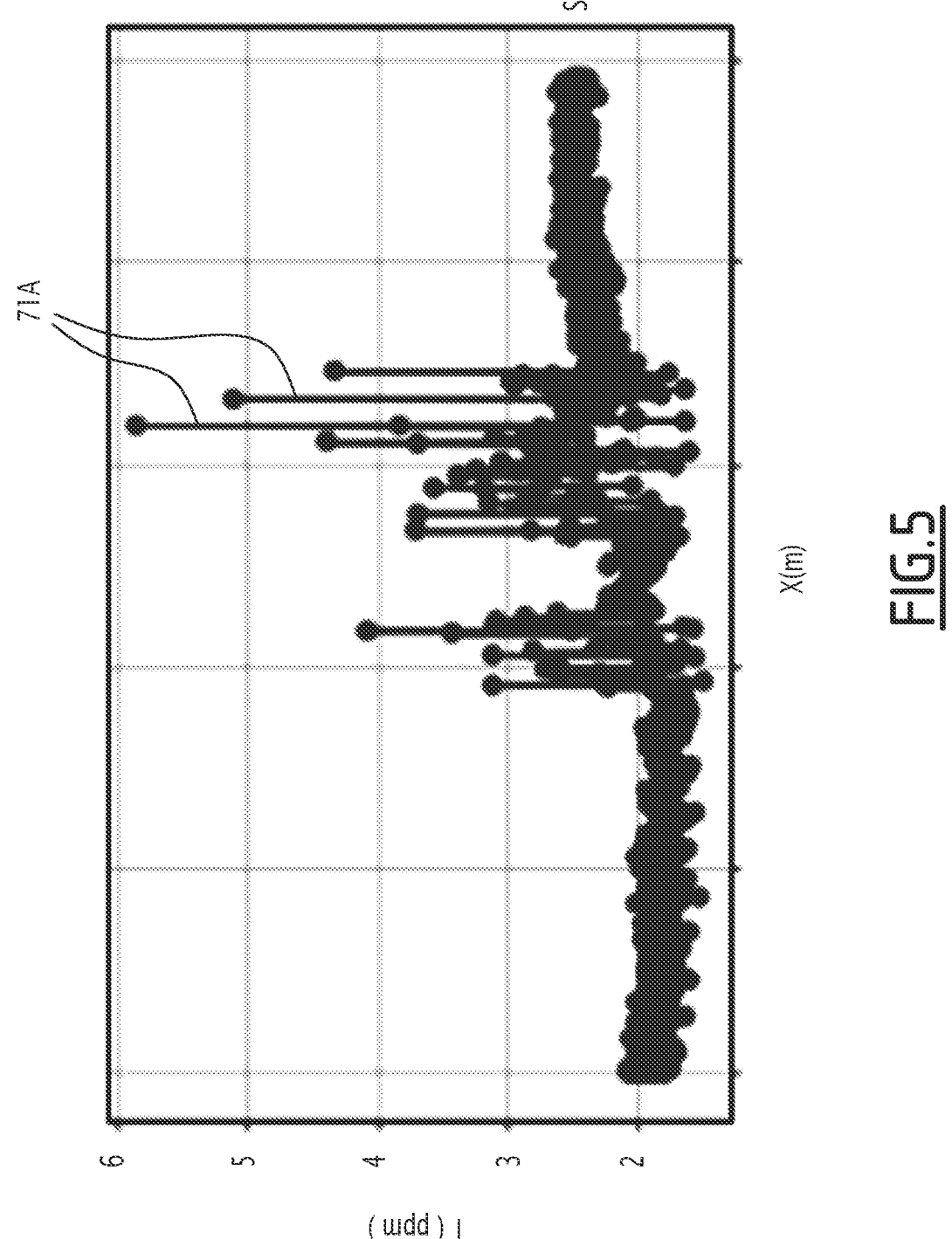
FIG. 5 is a view of the measurements carried out on a
horizontal line when implementing the flight plan from FIG.
4.

With reference to FIG. 1, the memory 68 contains a module 70 for obtaining and initially processing data representative of amounts of at least one gas in order to compute, on each parallel line 50, successive amounts of at least one gas along the parallel line 50, one example of which may be seen in FIG. 5.

The memory 68 furthermore contains a module 72 for integrating the amounts on each line 50 in the first direction D1 in order to obtain an integrated overall amount TGI on each line 50.

The memory 68 furthermore contains a module 74 for interpolating a curve 75 of integrated overall amounts TGI along the second direction D2 transverse to the first direction D1 (see FIG. 6), based on the integrated overall amounts TGI computed on each line 50, and a module 76 for integrating the product of the integrated overall amount TGI in the first direction and a wind speed V, the integration being carried out in the second direction D2, in order to maintain a raw flow Qb of gas flowing in the plume 16.

The memory 68 also contains a module 78 for determining a flow Qg of gas emitted by the source 14 by correcting the raw flow of gas Qb as a function of the structure of the plume to obtain.

The obtaining and processing module 70 is able to receive the data representative of the measured amounts of at least one gas, preferably of at least two gases, along each line 50, as measured by the drone 22 at each measurement point, in association with the geographical position X of the measurement point along the line 50.

It is able to transform the measured representative data into amounts of each of the gases at each measurement point X on each line 50 on the basis of a calibration curve associated with each gas.

A curve 71 of amounts T of each gas as a function of a first coordinate X along the line 50 in the direction D1 is thus obtained, as illustrated in FIG. 5.

The obtaining and processing module 70 is furthermore possibly able to filter the obtained amounts.

According to a first method, the obtaining and processing module 70 is able to detect amount peaks 71A on each curve 71, on the basis of a predetermined threshold S for the occurrence of a peak, and then to eliminate the observed peaks 71A from the obtained curve in order to obtain a curve of background values as a function of the first coordinate X.

In one variant, the obtaining and processing module 70 is able to implement an iterative algorithm in which the average value of the amounts along the line 50 is computed, and then in which all of the amounts above the average value are eliminated from the curve 71, and then to repeat the steps of computing the average value and of subtracting amounts above the average value until a convergence criterion is met.

The convergence criterion is for example that the difference between the successive average values between two iterations is less than a predetermined value, for example less than 10%.

A continuous background is thus determined and is subtracted from the curve 71 representing the amounts T as a function of the position X on each line 50.

The integration module 72 is able to integrate the curve 71 representing the amounts of each gas along each line 50, in the first direction D1, over the entire width of the line 50 in order to obtain an integrated overall amount TGI on each line 50, using the following equation:

$$TGI = \int_{Xmin}^{Xmax} T(X)dX$$

where X min and X max are the geographical coordinates characterizing the limits of the plume as defined along the extent E1 of the plume parallel to the first direction D1.

According to the first data processing method performed by the module 70, the integral of the curve of the background values is also computed and is subtracted from the previous integral.

According to the second method, the curve of background values is subtracted from the curve 70 of the amounts before integration.

Thus, for each line 50 in which a measurement has taken place, corresponding to a coordinate Z in the second direction D2, an integrated overall amount TGI(Z) is obtained.

Figure 6:
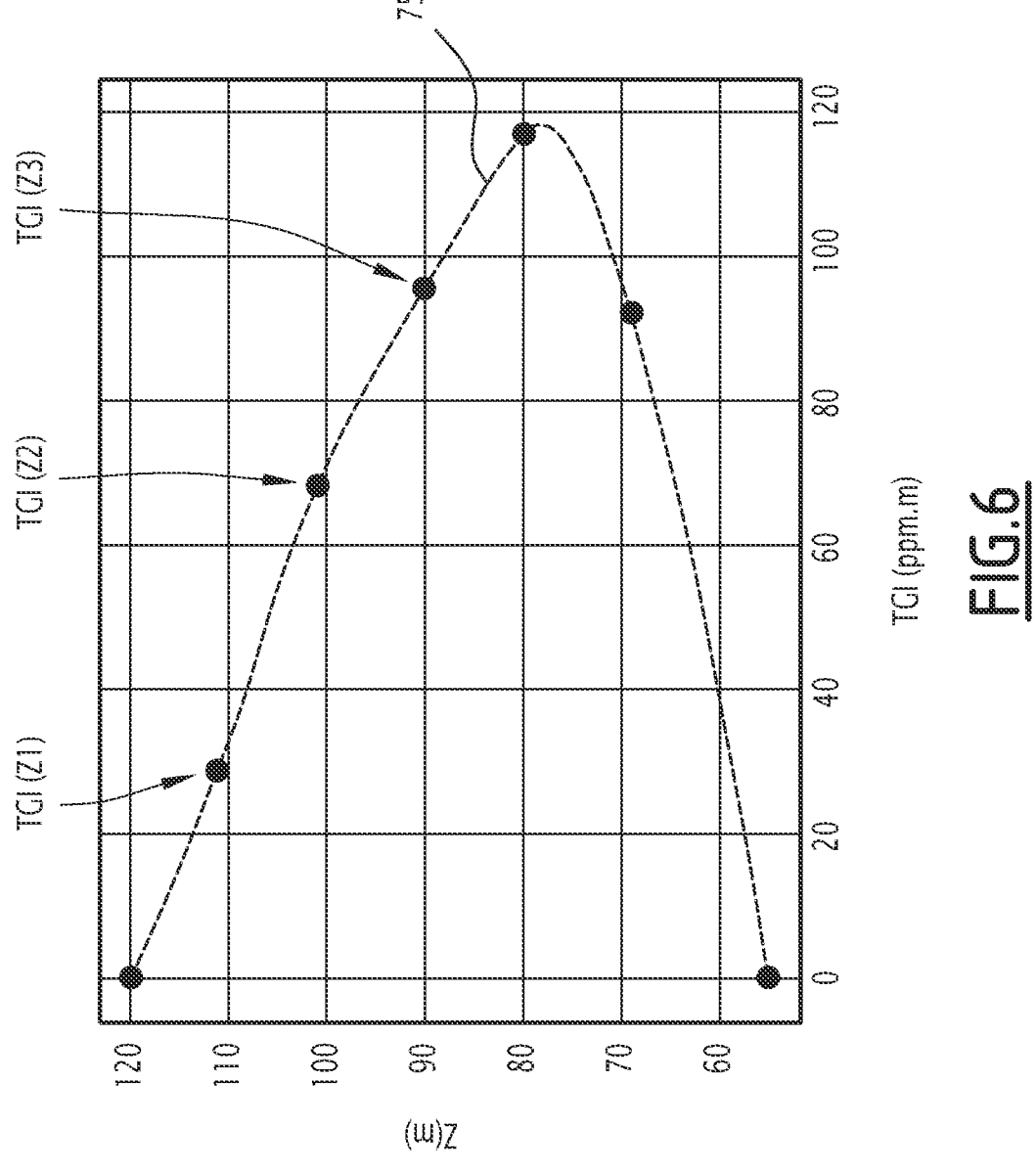
FIG. 6 is a view of a curve linking integrated amounts
obtained from multiple lines as a function of altitude, and the
interpolation performed between these amounts.

The interpolation module 74 is able to interpolate, based on the integrated overall amounts TGI(Z) on each line 50, in combination with their coordinates Z in the second direction, a continuous curve 75 of integrated overall amounts TGI as a function of the coordinate Z in the second direction D2, as illustrated by FIG. 6. The interpolated curve 75 is for example obtained using a cubic interpolation, in particular a piecewise cubic interpolation until convergence.

The integration module 76 is able to integrate the product of the wind speed V(Z) measured or obtained at each coordinate Z along the second direction D2 with the integrated overall amount TGI(Z) corresponding to this coordinate, obtained from the interpolated curve 75, in order to obtain a raw flow Qb passing through the measuring plane Pm using the following formula:

$$Qb = \int_{Zmin}^{Zmax} V(Z) \times TGI(Z) dZ$$

where Zmin and Z max are the minimum and maximum coordinates along the second direction D2 for which a line 50 of measurements was obtained.

Figure 2:
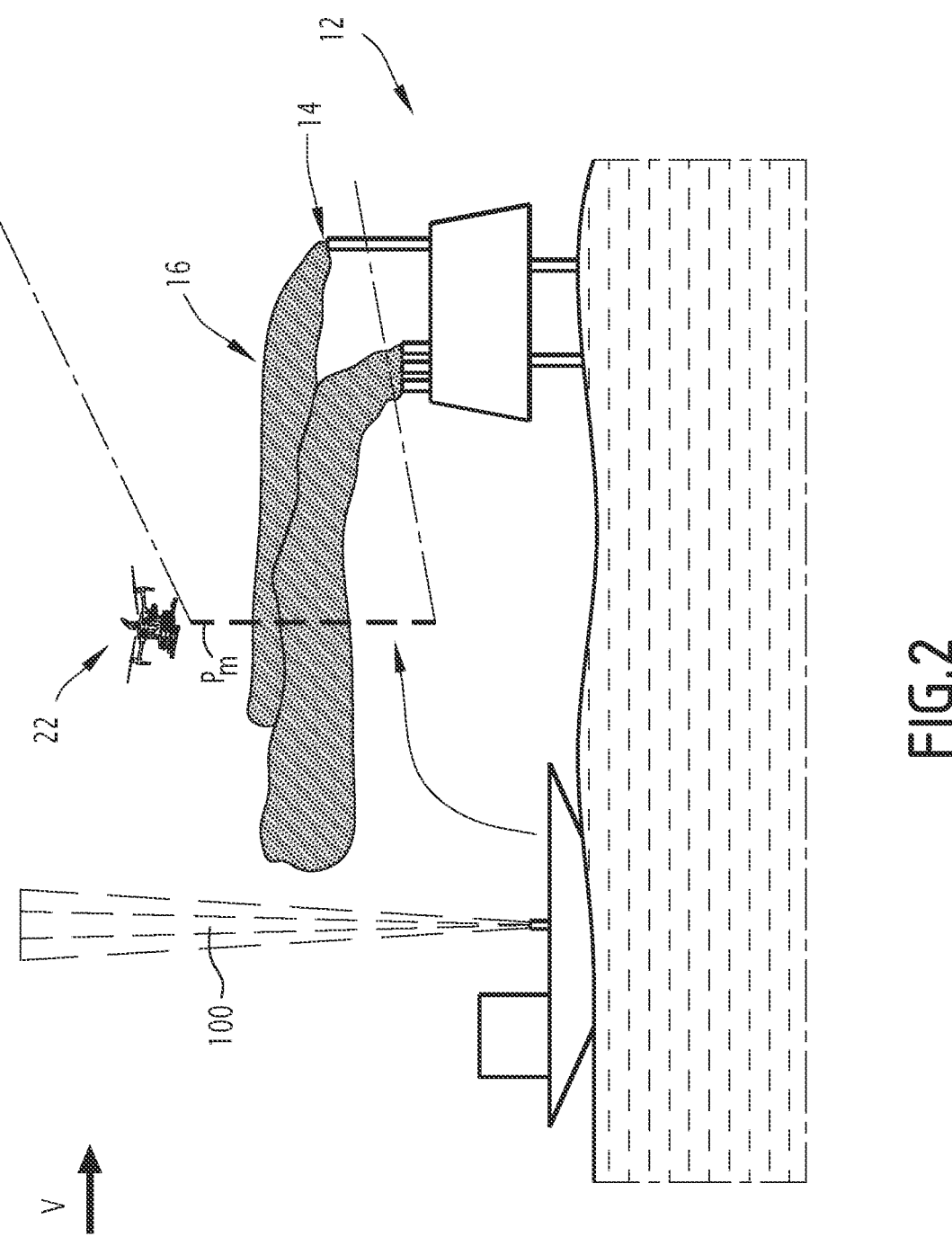
FIG. 2 is a view of a gas source within an installation, and
of the plume emitted by the gas source.

In the example illustrated by FIG. 2, the wind speed V(Z) is taken as a constant average wind speed along the second coordinate Z.

Figure 7:
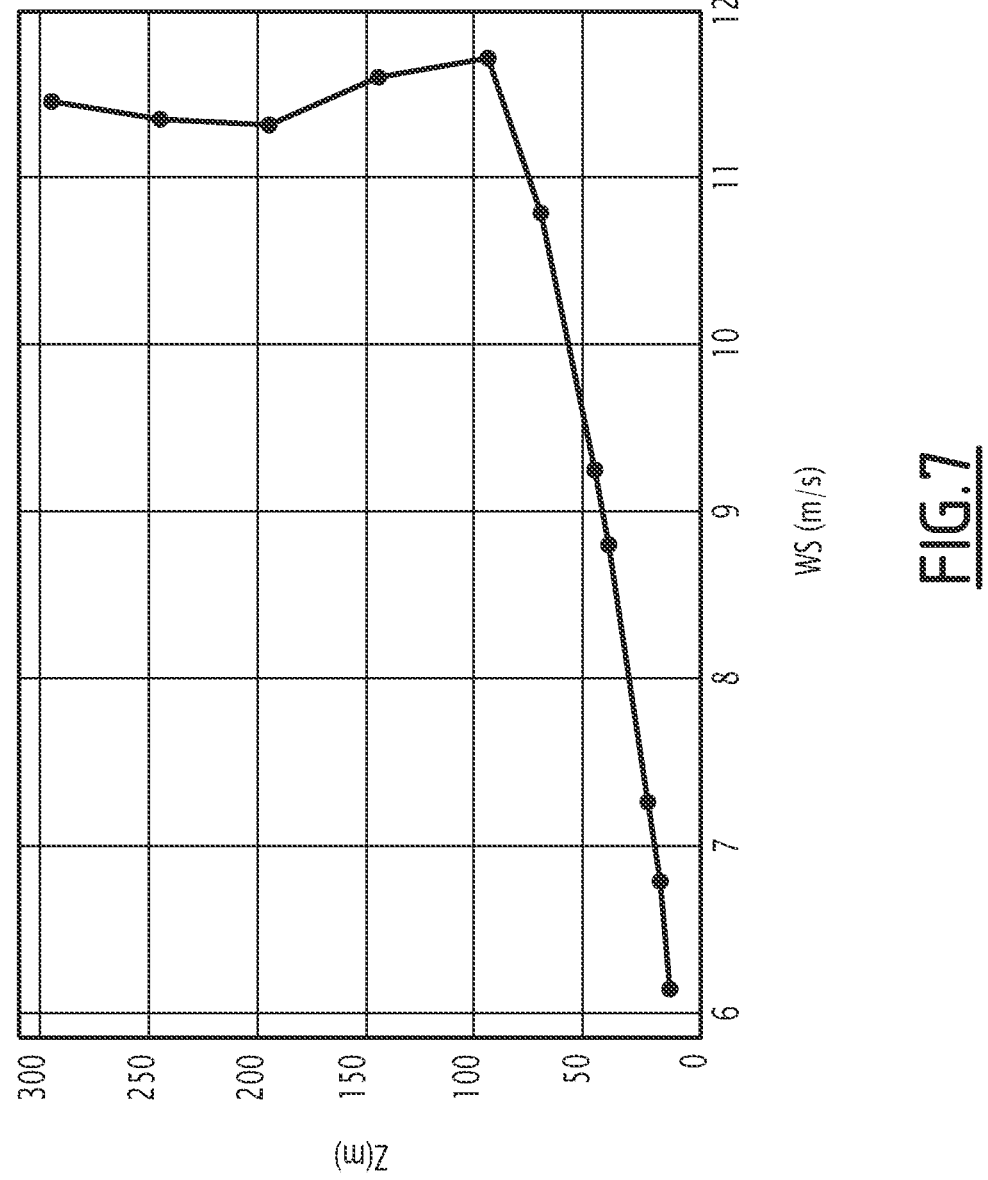
FIG. 7 is a view of an estimate of wind speed as a function
of altitude, able to be used in the implementation of the
method according to the invention.

As a variant, a curve of wind V(Z) as a function of the second coordinate along the second direction Z is established, as illustrated by FIG. 7, and the wind speed V(Z) at each second coordinate Z is used to compute the product with the integrated overall amount TGI(Z) at the second coordinate Z and carry out the integration.

The integration module 76 is thus able to obtain a total raw flow Qb of each measured gas passing through the measuring plane Pm, which may be seen in FIG. 3.

Next, the determination module 78 is able to correct the value of the measured total raw flow Qb in order to take into account the structure of the plume 16.

For example, if the measuring plane Pm is vertical, an angle of incline α of the direction of the flow in the plume 16 in the measuring plane Pm is computed, as a function of a value of the height of the rise area 18, and of an assumed plume shape in the transport area 20, computed as a function of the wind.

A total gas flow Qt passing through a plane Pp perpendicular to the flow direction is then computed on the basis of the raw flow Qb computed by the integration module 76 and of the determined angle of incline a, for example assuming that the cross section of the plume is circular perpendicular to the flow.

According to the principle of the conservation of mass, the flow of gas Qg emitted by the source 14 is then equal to the flow passing through the plane Pp.

A measuring method will now be described. Initially, the drone 22 is put into flight in order to take a path following a ladder-shaped movement in a measuring plane Pm, as illustrated by FIG. 4.

As indicated above, the drone 22 moves along a plurality of lines 50 parallel to a first direction D1 with a connecting segment 52 between each pair of adjacent parallel lines 50, the connecting segment 52 following a second direction D2 transverse to the first direction D1.

The data representative of the amounts of at least one gas, preferably of at least two gases, are collected by the measuring assembly 34 along each line 50.

The measurements are carried out continuously along the line 50.

The memory of the data collection unit stores the data representative of each amount of each gas, in association with the geographical position X along each line 50.

Next, while the drone 22 is flying or after the drone 22 has flown, the remote transmission system 38 exports data to the computing system 24 on the ground.

The obtaining and processing module 70 receives the data representative of the measured amounts of at least one gas, preferably of at least two gases, along each line 50, as measured by the drone 22 at each measurement point, in association with the geographical position X of the measurement point along the line 50.

It transforms the representative data into amounts of each of the gases at each measurement point X on each line 50 on the basis of a calibration curve associated with each gas. For each line 50, a curve 71 of amounts of each gas as a function of a first coordinate X along the line 50 in the direction D1 is thus obtained, as may be seen in FIG. 4.

The obtaining and processing module 70 possibly filters the obtained amounts, for example using the first method or the second method described above.

Next, the integration module 72 integrates the curve 71 representing the amounts of each gas along each line 50, in the first direction T1, over the entire width of the line 50 in order to obtain an integrated overall amount TGI on each line 50, using the equation given above:

$$TGI = \int_{Xmin}^{Xmax} T(X) dX$$

According to the first data processing method performed by the module 70, the integral of the curve of the background values is also computed and is subtracted from the previous integral.

According to the second method, the curve of background values is subtracted from the curve 70 of the amounts before integration.

Thus, for each line 50 in which a measurement has taken place, corresponding to a coordinate Z in the second direction D2, an integrated overall amount TGI(Z) is obtained.

The interpolation module 74 then interpolates, based on the integrated overall amounts TGI on each line 50, in combination with their coordinates Z in the second direction, a continuous curve 75 of integrated overall amounts TGI as a function of the coordinate Z in the second direction D2, as illustrated by FIG. 5. The interpolated curve 75 is for example obtained using a cubic interpolation, in particular a piecewise cubic interpolation until convergence.

The integration module 76 then integrates the product of the wind speed V(Z) measured or obtained at each coordinate Z along the second direction D2 with an integrated overall amount TGI(Z) corresponding to this coordinate (Z), obtained from the interpolated curve 75, in order to obtain a raw flow Qb passing through the measuring plane using the following formula:

$$Qb = \int_{Zmin}^{Zmax} V(Z) \times TGI(Z) dZ$$

In the example illustrated by FIG. 2, the wind speed V(Z) is taken as a constant average wind speed along the second coordinate Z.

As a variant, a curve of wind V(Z) as a function of the second coordinate along the second direction Z is established, as illustrated by FIG. 7, and the wind speed V(Z) at each second coordinate Z is used to compute the product with the integrated overall amount TGI(Z) at the second coordinate Z and carry out the integration.

The integration module 76 thus obtains a total raw flow Qb of each measured gas passing through the measuring plane Pm.

Next, the correction module 78 corrects the value of the measured total raw flow Qb in order to take into account the structure of the plume 16, as described above.

For example, if the measuring plane Pm is vertical, an angle of incline a of the direction of the flow in the plume 16 in the measuring plane Pm, along with a speed of change of the plume 16 in the measuring plane Pm, are computed as a function of a value of the height of the rise area 18, and of an assumed plume shape in the transport area 20.

A total gas flow Qg passing through a plane Pp perpendicular to the flow direction is then computed on the basis of the raw flow Qb computed by the integration module 76 and of the determined angle of incline a and of the computed speed of change of the plume 16, for example assuming that the cross section of the plume is circular perpendicular to the flow. The speed of change is computed along the axis of the plume and corresponds to the norm of the speed vector of the plume, which is perpendicular to the plane Pp.

According to the principle of the conservation of mass, the flow Qg of gas emitted by the source 14 is then equal to the flow passing through this plane.

The measuring method according to the invention is therefore particularly easy to implement, since it requires a simple measuring campaign using a drone 22 flying directly into the plume 16, at a distance from the source 14.

Following this measuring campaign, the computation is simple and effective in order to obtain an accurate determination of the flow emitted by the source 14.

This method is able to be implemented close to various industrial installations 12, even if these installations are inaccessible or/and require safety precautions. The measurements may be performed at low cost and frequently, thereby making it possible especially to track the evolution of emissions brought about by the source 14, and to ensure that they are under control or that they are reduced.

In one variant, shown in FIG. 8, for low-wind conditions, the plume 16 has a vertical configuration and the measuring plane Pm is a horizontal plane. The first direction D1 is then a horizontal direction, and the second direction D2 is a horizontal direction perpendicular to the first direction D1. The measuring process, including the measuring method, remain similar to those described above.

Advantageously, the measuring method according to the invention comprises an initial step of determining structural characteristics of the plume 16, for example by measuring the wind rose applicable to the source 14 at the time of the measuring campaign.

In another variant, the wind speed is measured directly right at the installation 12, for example by a lidar wind measuring device 100, as illustrated by FIG. 2.

As a variant, the wind speed is measured by a sensor carried by the drone 22, when the drone 22 is present on each line 50, or even advantageously at each point of measurement of an amount of gas on a line 50 by the drone 22.

Advantageously, the wind speed is measured at a plurality of successive times, preferably corresponding to the times of measurement of an amount of gas on each line 50.

In these variants, the integration module 72 is able to integrate the curve representing the products T(X, Z) x V(X, Z) of the amounts T(X, Z) of each gas read at each measurement point along each line 50, in the first direction D1, over the entire width of the line and the wind speed V(X, Z) at the measurement point, in order to obtain an integrated overall product PGI(Z) on each line 50, using the following equation:

$$PGI(Z) = \int_{Xmin}^{Xmax} T(X,Z) \times V(X,Z) dX$$

where X min and X max are the geographical coordinates characterizing the limits of the plume as defined along the extent E1 of the plume parallel to the first direction D1.

Advantageously, as described above, a curve of wind V(Z, t) as a function of the second coordinate in the second direction Z is established at a plurality of successive times t. The wind speed V(X, Z) used to compute the product with the measured amount T(X, Z) is chosen to be equal to the wind speed V(Z, t) measured at the second coordinate Z of the line 50 on which the amount T(X, Z) is measured, at the time closest to the time of measurement of the amount T(X, Z).

When the wind speed V(X, Z) is measured by a sensor carried by the drone 22, the wind speed V(X, Z) is preferably measured upon each measurement of the amount T(X, Z).

The product T(X, Z) x V(X, Z) is thus obtained at each measurement point on each line 50 using measured values of T(X) and V(X, Z).

According to the first data processing method performed by the module 70, the integral of the curve of the background values is also computed and is subtracted from the previous integral.

According to the second method, the curve of background values is subtracted from the curve 70 of the amounts before integration.

Thus, for each line 50 in which a measurement has taken place, corresponding to a coordinate Z in the second direction D2, an integrated overall product PGI(Z) is obtained.

The interpolation module 74 is able to interpolate, based on the integrated overall products PGI(Z) on each line 50, in combination with their coordinates Z in the second direction, a continuous curve of integrated overall products PGI as a function of the coordinate Z in the second direction D2. The interpolated curve is for example obtained using a cubic interpolation, in particular a piecewise cubic interpolation until convergence.

The integration module 76 is able to integrate the integrated overall products obtained from the interpolated curve 75 in order to obtain a raw flow Qb passing through the measuring plane Pm using the following formula:

$$Qb = \int_{Zmin}^{Zmax} PGI(Z) dZ$$

where Zmin and Z max are the minimum and maximum coordinates along the second direction D2 for which a line 50 of measurements was obtained.

The integration module 76 is thus able to obtain a total raw flow Qb of each measured gas passing through the measuring plane Pm, which may be seen in FIG. 3.

The methods that are described as a variant greatly improve the accuracy of the measurement of the total raw flow Qb, while retaining simple integration in comparison with Kriging methods.

Moreover, the total raw measurement Qb is more accurate if the wind speed changes rapidly or if an optical present between the source 14 and a line 50 affects the wind speed on the line 50.

The invention claimed is:

1. A method to compute a flow of at least one gas emitted by a source into the atmosphere, implemented by a computer, comprising:

retrieving amount data relative to amounts of at least one gas, said amount data being measured in the atmosphere at a distance from the source along a plurality of lines parallel to a first direction;

integrating first quantities which are the amounts retrieved on each line in the first direction to obtain a first integrated overall quantity which is an integrated overall amount on each line;

interpolating a curve of first integrated overall quantities as a function of a coordinate in a second direction perpendicular to the first direction, based on the first integrated overall quantities;

integrating a second quantity which is a product of the integrated overall amounts on each line obtained from the interpolated curve and a wind speed present on the line, in the second direction, to obtain a raw flow of gas; and determining the flow of gas emitted by the source based on the raw flow of gas.

2. The method according to claim 1, wherein interpolating the curve is carried out using a cubic interpolation.

3. The method according to claim 1, comprising preliminarily retrieving data about the wind speeds present on each line.

4. The method according to claim 1, comprising preliminarily determining an average wind common to all of the lines.

5. The method according to claim 1, comprising, after retrieving the amount data, computing a continuous background of gas present in the atmosphere and processing the amount data in order to eliminate the continuous background.

6. The method according to claim 5, wherein determining the continuous background comprises, for each line, computing an average value of amounts, measured on the line, and then eliminating amounts above the average value, and repeating the computing an average value of amounts and eliminating amounts above the average value until the difference between two successive average values is less than a convergence threshold.

7. The method according to claim 1, wherein the first direction is horizontal, and the second direction is vertical.

8. The method according to claim 1, wherein the raw flows of at least two gases emitted by the source are computed.

9. A method to measure emissions of a source into the atmosphere, comprising:

collecting amounts of at least one gas in the atmosphere at a distance from the source along a plurality of lines parallel to a first direction by flying a drone equipped to measure data representative of amounts of at least one gas;

transferring the collected data representative of the amounts of at least one gas to a computer;

the computer implementing the computing method according to claim 1.

10. The method according to claim 9, comprising preliminarily determining a wind direction and/or a configuration of an emission plume downstream of the source, the drone being flown based on the predetermined plume configuration.

11. The method according to claim 9, comprising measuring the wind speed.

12. The method according to claim 11, wherein the wind speed is measured at a plurality of successive times.

13. The method according to claim 12, wherein the wind speed is measured by a sensor carried by the drone.

14. A system to compute a flow of at least one gas emitted by a source into the atmosphere, the system comprising a configuration to:

obtain amount data about amounts of at least one gas, said data being measured in the atmosphere at a distance from the source along a plurality of lines parallel to a first direction;

integrate first quantities which are the amounts retrieved on each line in the first direction to obtain a first integrated overall quantity which is an integrated overall amount on each line;

interpolate a curve of first integrated overall quantities as a function of a coordinate in a second direction perpendicular to the first direction, based on the first integrated overall quantities;

integrate a second quantity which is an amount of the integrated overall amounts on each line obtained from the interpolated curve and a wind speed present on the line, in the second direction, to obtain a raw flow of gas;

determine the flow of gas emitted by the source based on the raw flow of gas.

15. A kit to measure the emissions of at least one gas by a source into the atmosphere, comprising:

a drone configured to fly in the atmosphere at a distance from the source along a plurality of lines parallel to a first direction;

the drone being configured to measure data representative of amounts of at least one gas along each line parallel to the first direction;

a computer according to claim 14, configured to receive the data representative of amounts of at least one gas measured by the drone.

16. The kit according to claim 15, wherein the drone is configured to continuously measure data representative of amounts of at least two gases present in the atmosphere.

17. The method according to claim 12 wherein the wind speed used to compute the second quantity is measured at a time of measurement of the amount of at least one gas on the line that is used to compute the first quantity.

18. The kit according to claim 16, comprising a sensor configured to continuously measure wind speed, the sensor being carried by the drone.

19. A method to compute a flow of at least one gas emitted by a source into the atmosphere, implemented by a computer, comprising:

retrieving amount data relative to amounts of at least one gas, said amount data being measured in the atmosphere at a distance from the source along a plurality of lines parallel to a first direction;

integrating first quantities each of which is a product of an amount retrieved at a point on each line in the first direction and wind speed present at the point to obtain a first integrated overall quantity which is an integrated overall amount on each line;

interpolating a curve of first integrated overall quantities as a function of a coordinate in a second direction perpendicular to the first direction, based on the first integrated overall quantities;

integrating a second quantity which is an integrated overall product of the first integrated overall quantities obtained from the interpolated curve, in the second direction, to obtain a raw flow of gas;

determining the flow of gas emitted by the source based on the raw flow of gas.

20. A method to compute a flow of at least one gas emitted by a source into the atmosphere, implemented by a computer, comprising:

retrieving amount data relative to amounts of at least one gas, said amount data being measured in the atmosphere at a distance from the source along a plurality of lines parallel to a first direction;

computing a continuous background of gas present in the atmosphere and processing the amount data to eliminate the continuous background;

integrating first quantities computed based on the processed amount data that the continuous background has been eliminated from the amounts retrieved on each line in the first direction and/or on wind speeds present on the line to obtain a first integrated overall quantity on each line;

interpolating a curve of first integrated overall quantities as a function of a coordinate in a second direction perpendicular to the first direction, based on the first integrated overall quantities;

integrating a second quantity computed based on first integrated overall quantities obtained from the interpolated curve and/or a wind speed present on the line, in the second direction, to obtain a raw flow of gas;

determining the flow of gas emitted by the source based on the raw flow of gas.

* * * * *

14